United States Patent
Fei et al.

(10) Patent No.: US 9,370,472 B2
(45) Date of Patent: Jun. 21, 2016

(54) FLOWABLE PEROXIDE CONTAINING ORAL CARE COMPOSITIONS

(71) Applicant: Colgate-Palmolive Company, New York, NY (US)

(72) Inventors: Lin Fei, Kendall Park, NJ (US); Suman Chopra, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/651,134

(22) PCT Filed: Dec. 14, 2012

(86) PCT No.: PCT/US2012/069855
§ 371 (c)(1),
(2) Date: Jun. 10, 2015

(87) PCT Pub. No.: WO2014/092733
PCT Pub. Date: Jun. 19, 2014

(65) Prior Publication Data
US 2015/0328092 A1    Nov. 19, 2015

(51) Int. Cl.
*A61K 8/22* (2006.01)
*A61K 8/37* (2006.01)
*A61K 8/49* (2006.01)
*A61Q 11/00* (2006.01)
*A61K 8/81* (2006.01)
*A61K 8/24* (2006.01)
*A61K 8/34* (2006.01)
*A61K 8/86* (2006.01)

(52) U.S. Cl.
CPC ... *A61K 8/22* (2013.01); *A61K 8/24* (2013.01); *A61K 8/345* (2013.01); *A61K 8/375* (2013.01); *A61K 8/4993* (2013.01); *A61K 8/8176* (2013.01); *A61K 8/86* (2013.01); *A61Q 11/00* (2013.01); *A61K 8/8182* (2013.01); *A61K 2800/48* (2013.01); *A61K 2800/57* (2013.01); *A61K 2800/594* (2013.01)

(58) Field of Classification Search
USPC ............................................. 424/53
See application file for complete search history.

(56) References Cited

U.S. PATENT DOCUMENTS

| | | | |
|---|---|---|---|
| 5,296,215 A * | 3/1994 | Burke | A61K 8/466 424/49 |
| 5,776,435 A | 7/1998 | Gaffar et al. | |
| 6,890,894 B2 * | 5/2005 | Connor | A61K 8/361 510/501 |
| 2005/0036956 A1 | 2/2005 | Fei et al. | |
| 2006/0045854 A1* | 3/2006 | Zaidel | A61K 8/0208 424/53 |
| 2006/0062744 A1 | 3/2006 | Lokken | |
| 2007/0071695 A1 | 3/2007 | Chopra et al. | |
| 2008/0081023 A1 | 4/2008 | Decknet et al. | |
| 2012/0282192 A1 | 11/2012 | Miller et al. | |
| 2013/0287710 A1 | 10/2013 | Chopra et al. | |

FOREIGN PATENT DOCUMENTS

| DE | 102004041333 | 3/2006 |
|---|---|---|
| WO | WO 2012/018588 | 2/2012 |
| WO | WO 2012/102750 | 8/2012 |

OTHER PUBLICATIONS

Polymer-Surfactant Interaction, Feb. 16, 2006; Figures and Description, in particuar Figures 1, 2, 7, 12, 19, 20, 22, 23, 40 and Description.

International Search Report and Written Opinion in International Application No. PCT/US2012/069855, mailed Oct. 10, 2013.

Written Opinion in International Application No. PCT/US2012/069855, mailed Jan. 16, 2015.

* cited by examiner

*Primary Examiner* — Walter Webb

(57) ABSTRACT

Described herein are oral care compositions comprising (i) a whitening complex comprising crosslinked polyvinylpyrrolidone complexed with hydrogen peroxide, and (ii) a thickening agent comprising a crosslinked polyvinylpyrrolidone, the composition further comprising (iii) a nonionic rheology modifier selected from at least one of a polysorbate surfactant and an alkylene glycol ester of a $C_6$-$C_{12}$ fatty acid, or a mixture thereof.

31 Claims, No Drawings

FLOWABLE PEROXIDE CONTAINING ORAL CARE COMPOSITIONS

BACKGROUND

Dentifrice formulations comprising peroxide are known and useful for cleaning and whitening teeth. Formula modifications made to stabilize single phase peroxide containing compositions may result in compositions which are difficult to pump during the manufacturing process.

There is thus a need for improved single phase peroxide containing compositions, for example dentifrice compositions, which not only exhibit cosmetic stability of the peroxide, and so are stable for long-term storage and are suitable for everyday consumer use, but also have rheological properties which make them easy to pump during manufacture and packaging.

SUMMARY

The invention at least partly aims to meet that need.

The invention also aims to provide a single phase whitening oral care composition, which not only exhibits cosmetic stability of the peroxide, and so is stable for long-term storage and is suitable for everyday consumer use, but also has rheological properties which make the composition easy to pump during manufacture and packaging of the composition.

The invention further aims to provide a single phase whitening oral care composition that is stable during long term storage and remains effective to clean and whiten teeth.

Accordingly, the invention provides an oral care composition comprising (i) a whitening complex comprising crosslinked polyvinylpyrrolidone complexed with hydrogen peroxide, and (ii) a thickening agent comprising a crosslinked polyvinylpyrrolidone, the composition further comprising (iii) a nonionic rheology modifier selected from at least one of a polysorbate surfactant and an alkylene glycol ester of a $C_6$-$C_{12}$ fatty acid, or a mixture thereof.

Optionally, the polysorbate surfactant is selected from polysorbate 20 and polysorbate 80, or a mixture thereof.

Optionally, the alkylene glycol ester of a $C_6$-$C_{12}$ fatty acid comprises a propylene glycol ester of a $C_6$-$C_{12}$ fatty acid. Optionally, the alkylene glycol ester of a $C_6$-$C_{12}$ fatty acid comprises an alkylene glycol ester of caprylic acid. Typically, the alkylene glycol ester of caprylic acid comprises propylene glycol monocaprylate.

Optionally, the nonionic rheology modifier comprises from 0.5 to 4 wt %, further optionally from 1 to 3 wt %, based on the weight of the composition. Typically, the nonionic rheology modifier comprises about 2 wt % based on the weight of the composition.

Optionally, the crosslinked polyvinylpyrrolidone thickening agent is present in an amount of from 3 wt % to 8 wt %, further optionally from 5 wt % to 7 wt %, based on the weight of the composition.

In some embodiments, the crosslinked polyvinylpyrrolidone thickening agent is present in an amount of from 5 wt % to 7 wt % based on the weight of the composition, the nonionic rheology modifier comprises from 1 to 3 wt % based on the weight of the composition, and the total weight of the crosslinked polyvinylpyrrolidone thickening agent and the nonionic rheology modifier is from 7 wt % to 9 wt % based on the weight of the composition.

In some embodiments, the composition further comprises an ethylene oxide, propylene oxide block co-polymer of average molecular weight greater than 5000 Da, being substantially free of an ethylene oxide, propylene oxide block co-polymer of average molecular weight less than 5000 Da. Typically, the ethylene oxide, propylene oxide block co-polymer comprises (ethylene oxide)$_x$-(propylene oxide)$_y$ wherein x is an integer of 80-150 and y is an integer 30-80. Optionally, the ethylene oxide, propylene oxide block co-polymer is present in an amount of from 5 wt % to 10 wt % based on the weight of the composition.

Optionally, the crosslinked polyvinylpyrrolidone complexed with hydrogen peroxide is present in an amount of from 3 wt % to 8 wt % based on the weight of the composition. Optionally, the whitening complex contains 10-30 wt % hydrogen peroxide and 5-15 wt % total nitrogen, based on the weight of the whitening complex. Optionally, the total amount of hydrogen peroxide is from 0.5 wt % to 3 wt % based on the weight of the composition.

In some embodiments, the composition further comprises polyethylene glycol of average molecular weight 400 to 800 Da. Optionally, the polyethylene glycol is present in an amount of from 5 wt % to 15 wt % based on the weight of the composition In some embodiments, the composition further comprises at least one humectant selected from glycerin and propylene glycol, or a mixture thereof. Optionally, the at least one humectant is present in an amount of from 35 wt % to 50 wt %, further optionally from 40 wt % to 45 wt %, based on the weight of the composition.

In some embodiments, the composition comprises propylene glycol in an amount of from 10 wt % to 25 wt % based on the weight of the composition. In some embodiments, the composition comprises glycerin in an amount of from 25 wt % to 40 wt % based on the weight of the composition.

Optionally, the composition contains less than 3 wt % water based on the weight of the composition.

In some embodiments, the composition is a toothpaste comprising a calcium pyrophosphate abrasive. Optionally, the calcium pyrophosphate is present in an amount of from 10 wt % to 20 wt % based on the weight of the composition.

In some embodiments, the composition comprises the following ingredients by weight, each being based on the weight of the composition:

| | |
|---|---|
| a. Nonionic rheology modifier | 1-3% |
| b. Crosslinked polyvinylpyrrolidone | 5-7% |
| c. Glycerin | 30-35% |
| d. Propylene glycol | 12-18% |
| e. Ethylene oxide, propylene oxide block co-polymer, avg. MW >5 kDa | 5-10% |
| f. Polyethylene glycol 600 | 5-15% |
| g. Crosslinked polyvinylpyrrolidone complexed with 15-25% $H_2O_2$ | 3-8% |
| h. Calcium pyrophosphate | 10-20% |

In some embodiments, the composition further comprises an anionic surfactant in an amount of from 0.5 to 3 wt % based on the weight of the composition.

Optionally, the anionic surfactant and the nonionic rheology modifier constitute the sole surfactants in the composition In the preferred embodiments of the invention, the oral care compositions are stable during long term storage and remain effective to clean and whiten teeth, and in addition the oral care compositions have rheological properties which render them readily pumpable under typical processing conditions encountered during commercial manufacture, with good cosmetic stability during manufacture and use of the compositions.

The invention also provides a method of tooth whitening comprising applying the composition of the invention to the surface of a mammalian tooth.

Further embodiments of the invention will be apparent from the detailed description and the examples.

DETAILED DESCRIPTION

As used throughout, ranges are used as shorthand for describing each and every value that is within the range. Any value within the range can be selected as the terminus of the range.

In some embodiments, the present invention provides an oral care composition comprising (i) a whitening complex comprising crosslinked polyvinylpyrrolidone complexed with hydrogen peroxide, and (ii) a thickening agent comprising a crosslinked polyvinylpyrrolidone, the composition further comprising (iii) a nonionic rheology modifier selected from at least one of a polysorbate surfactant and an alkylene glycol ester of a $C_6$-$C_{12}$ fatty acid, or a mixture thereof.

In some embodiments, the invention provides a toothpaste comprising an abrasive, e.g., a calcium abrasive. In other embodiments, the invention provides an abrasive-free gel.

Thickening System/Rheology Modifier

In some embodiments, the composition includes a rheology-modified thickening system in which a thickening agent is provided which thickens the composition to enable the composition to be extruded by a user from a container such as a tube to enable the composition to be used as a toothpaste or gel. The rheology-modified thickening system also includes a rheology modifier which reduces the dynamic yield shear stress of the composition, for example to no more than 10 bar, to enable the composition to be pumped at a relatively low pumping pressure, for example no more than 15 bar, during manufacture.

In some embodiments, the polysorbate surfactant is selected from polysorbate 20 and polysorbate 80, or a mixture thereof.

The chemical composition of polysorbate 20 is polyoxyethylene (20) sorbitan monolaurate. The chemical composition of polysorbate 80 is polyoxyethylene (20) sorbitan monooleate.

In some embodiments, the alkylene glycol ester of a $C_6$-$C_{12}$ fatty acid comprises a propylene glycol ester of a $C_6$-$C_{12}$ fatty acid. In some embodiments, the alkylene glycol ester of a $C_6$-$C_{12}$ fatty acid comprises an alkylene glycol ester of caprylic acid. Typically, the alkylene glycol ester of caprylic acid comprises propylene glycol monocaprylate.

Propylene glycol monocaprylate is a mixture of the propylene glycol monoesters and diesters of fatty acids composed predominately of caprylic acid (i.e. octanoic acid). Two types, Type I and Type II, of propylene glycol monocaprylate are available in commerce, and both Type I and Type II, independently or in admixture, may be employed in the composition of the invention. The requirements for monoester and diester content differ for the two types of propylene glycol monocaprylate, as set forth in the accompanying Table 1:

TABLE 1

|  | Content of Monoesters (wt %) | | Content of Diesters (wt %) | |
| --- | --- | --- | --- | --- |
|  | Min. | Max. | Min. | Max. |
| Type I | 55.0 | 80.0 | 20.0 | 45.0 |
| Type II | 90.0 | — | — | 10.0 |

In some embodiments, the nonionic rheology modifier comprises from 0.5 to 4 wt %, further optionally from 1 to 3 wt %, based on the weight of the composition. Typically, the nonionic rheology modifier comprises about 2 wt % based on the weight of the composition.

In some embodiments, the crosslinked polyvinylpyrrolidone thickening agent is present in an amount of from 3 wt % to 8 wt %, further optionally from 5 to 7 wt %, based on the weight of the composition.

In some embodiments, the crosslinked polyvinylpyrrolidone thickening agent is present in an amount of from 5 wt % to 7 wt % based on the weight of the composition, the nonionic rheology modifier comprises from 1 to 3 wt % based on the weight of the composition, and the total weight of the crosslinked polyvinylpyrrolidone thickening agent and the nonionic rheology modifier is from 7 wt % to 9 wt % based on the weight of the composition.

The compositions of the invention may optionally comprise an additional orally acceptable thickening agent, selected from one or more of, without limitation, carbomers, also known as carboxyvinyl polymers, carrageenans, also known as Irish moss and more particularly carrageenan (iota-carrageenan), high molecular weight polyethylene glycols (such as CARBOWAX®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, and colloidal magnesium aluminum silicate and mixtures of the same. Optionally, such additional thickening agents are present in a total amount of about 0.1 wt % to about 50 wt %, for example about 0.1 wt % to about 35 wt % or about 1 wt % to about 15 wt %, based on the weight of the composition.

Polymer Additives

In some embodiments, the composition further comprises polymer thickeners selected from (i) polyethylene glycol, (ii) polyethylene glycol—polypropylene glycol block co-polymers having a molecular weight of at least 5000, and (iii) combinations thereof.

In some embodiments, the composition comprises an ethylene oxide, propylene oxide block co-polymer of formula (ethylene oxide)$_x$-(propylene oxide)$_y$, wherein x is an integer of 80-150, e.g. 100-130, e.g. about 118, and y is an integer 30-80, e.g. about 60-70, e.g. about 66, having an average molecular weight of greater than 5000, e.g., 8000-13000 Da, e.g. about 9800;

In some embodiments, the composition comprises an ethylene oxide, propylene oxide block co-polymer of average molecular weight greater than 5000 Da, being substantially free of an ethylene oxide, propylene oxide block co-polymer of average molecular weight less than 5000 Da. Optionally, the ethylene oxide, propylene oxide block co-polymer is present in an amount of from 5 wt % to 10 wt % based on the weight of the composition. Block copolymers of ethylene oxide/propylene oxide are useful, but higher molecular weight, e.g., >5000 Da are preferred, e.g. including PLURACARE® L1220 (available from BASF, Wyandotte, Mich., United States of America).

In some embodiments, the composition further comprises polyethylene glycol of average molecular weight 400 to 800 Da, e.g., about 600 Da. Low or medium molecular weight polyethylene glycol, e.g., PEG 400, PEG 600, PEG 800, PEG 1000 and mixtures thereof are useful in the compositions of some embodiments of the invention.

Further optionally, the polyethylene glycol may be present in an amount of from 5 wt % to 15 wt % based on the weight of the composition.

In some embodiments, the oral care compositions may additionally comprise a stabilizing amount of an additional linear polyvinylpyrrolidone.

In some embodiments, the crosslinked polyvinylpyrrolidone complexed with hydrogen peroxide is present in an amount of from 3 wt % to 8 wt % based on the weight of the composition.

Typically, the whitening complex contains 10-30 wt % hydrogen peroxide and 5-15 wt % total nitrogen, based on the weight of the whitening complex. In some embodiments, the total amount of hydrogen peroxide is from 0.5 wt % to 3 wt % based on the weight of the composition, e.g., 0.75-1.5 wt %, e.g. about 1 wt %.

Typically, the whitening complex contains about 15-25%, for example about 17-22% of hydrogen peroxide by weight, and about 7-12% total nitrogen by weight; for example, having substantially the same specifications as Polyplasdone® XL-10, e.g., Polyplasdone® XL-10F, e.g., available from International Specialty Products (Wayne, N.J.).

Some embodiments further comprise an abrasive. Yet further embodiments provide oral care compositions comprising from about 5 to about 15 wt % abrasive based on the weight of the composition.

Where abrasives are present, the average particle size is generally about 0.1 to about 30 microns, for example about 1 to about 20 or about 5 to about 15 microns.

The abrasive may comprise a calcium abrasive, such as a calcium phosphate salt, e.g., calcium pyrophosphate, dicalcium orthophosphate dihydrate, tricalcium phosphate, and/or calcium polymetaphosphate. In a typical embodiment, the calcium abrasive comprises calcium pyrophosphate. In another embodiment, the calcium abrasive comprises calcium carbonate.

Optionally, the composition is a toothpaste comprising a calcium pyrophosphate abrasive. Further optionally, the calcium pyrophosphate is present in an amount of from 10 wt % to 20 wt % based on the weight of the composition.

The compositions of the invention may also comprise various dentifrice ingredients to adjust the rheology and feel of the composition such as humectants, surface active agents, or gelling agents, etc.

In some embodiments, the oral care composition comprises a vehicle for the active components. The vehicle may comprise humectants, e.g. selected from glycerin, propylene glycol or a combination thereof.

In some embodiments, the oral care composition comprises from about 35 to about 50 wt %, optionally from about 40 to about 45 wt % humectant based on the weight of the composition.

In some embodiments, the composition further comprises propylene glycol in an amount of from 10 wt % to 25 wt % based on the weight of the composition.

In some embodiments, the composition further comprises glycerin in an amount of from 25 wt % to 40 wt % based on the weight of the composition.

Typical compositions of the invention have a "low water" content, meaning that a total concentration of water, including any free water and all water contained in any ingredients, is less than about 5%, preferably less than 3%, preferably less than 2% water.

Optionally, the composition contains less than 3 wt % water based on the weight of the composition. In some embodiments, the oral care composition contains less than 2 wt % water, e.g., less than 1 wt % water. In some embodiments, the composition is substantially anhydrous.

It is preferred that the vehicle ingredients in particular provide a dentifrice with a viscosity of about 10,000 CPS to about 700,000 CPS, preferably about 30,000 CPS to about 300,000 CPS.

As recognized by one of skill in the art, the oral compositions of the invention optionally include other materials, such as for example, anti-caries agents, desensitizing agents, viscosity modifiers, diluents, surface active agents, such as surfactants, emulsifiers, and foam modulators, pH modifying agents, abrasives, in addition to those listed above, humectants, mouth feel agents, sweetening agents, flavor agents, colorants, preservatives, and combinations thereof. It is understood that while general attributes of each of the above categories of materials may differ, there may be some common attributes and any given material may serve multiple purposes within two or more of such categories of materials. Preferably, the carrier is selected for compatibility with other ingredients of the composition.

Flavorants, sweeteners, colorants, foam modulators, mouth-feel agents and others additively may be included if desired, in the composition.

The compositions of the present invention may comprise, in addition to the nonionic rheology modifier, a surface active agent (surfactant). Suitable surfactants include without limitation water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine.

In some embodiments, the composition may additionally comprise an anionic surfactant, e.g., sodium lauryl sulfate (SLS). In some embodiments, the composition further comprises an anionic surfactant in an amount of from 0.5 to 3 wt % based on the weight of the composition. In some embodiments the anionic surfactant and the nonionic rheology modifier constitute the sole surfactants in the composition.

The compositions of the present invention optionally comprise one or more further active material(s), which is or are operable for the prevention or treatment of a condition or disorder of hard or soft tissue of the oral cavity, the prevention or treatment of a physiological disorder or condition, or to provide a cosmetic benefit.

In various embodiments of the present invention, the oral composition comprises an anticalculus (tartar control) agent. Generally, tartar control agents are categorized as being incompatible with some whitening agents, but embodiments of the present invention incorporate tartar control agents and whitening agents in a single phase whitening composition.

Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. Typically, the anticalculus agent is present at about 0.1% to about 30 wt % based on the weight of the composition.

The oral composition may include a mixture of different anticalculus agents.

In some embodiments, the composition additionally comprises a tartar control agent, e.g., selected from tetrasodium pyrophosphate (TSPP) and sodium tripolyphosphate (STPP).

In one preferred embodiment, tetrasodium pyrophosphate (TSPP) and sodium tripolyphosphate (STPP) are used. The anticalculus agent comprises TSPP at about 1-2% and STPP at about 7% to about 10%, each based on the weight of the composition.

The oral care composition can optionally include at least one orally acceptable source of fluoride ions. Any known or to be developed in the art may be used. Suitable sources of fluoride ions include fluoride, monofluorophosphate and fluorosilicate salts. One or more fluoride ion-releasing compound is optionally present in an amount providing a total of about 100 to about 20,000 ppm, about 200 to about 5,000 ppm, or about 500 to about 2,500 ppm, fluoride ions, each based on the weight of the composition.

The compositions may include a stannous ion or a stannous ion source. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%, each based on the weight of the composition.

In some embodiments, the compositions of the invention optionally comprise an antimicrobial (e.g., antibacterial) agent, e.g., triclosan. A further illustrative list of useful antibacterial agents is provided in such as those listed in U.S. Pat. No. 5,776,435 to Gaffar et al., the contents of which are incorporated herein by reference. One or more antimicrobial agents are optionally present in an antimicrobial effective total amount, typically about 0.05% to about 10%, for example about 0.1% to about 3%, each based on the weight of the composition.

In some embodiments, the compositions of the invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the invention may optionally comprise a sialagogue or saliva-stimulating agent, an antiplaque agent, an anti-inflammatory agent, and/or a desensitizing agent.

While ingredients are sometimes identified herein by category, e.g., humectant, antioxidant, thickener, etc., this identification is for convenience and clarity, but is not intended to be limiting. All of the ingredients in the compositions may have functions in addition to their primary function, and may contribute to the overall properties of the composition, including its stability, efficacy, consistency, mouthfeel, taste, odor and so forth.

In some embodiments, the composition comprises the following ingredients by weight, each being based on the weight of the composition:

| Ingredient | Amount |
|---|---|
| Nonionic rheology modifier | 1-3% |
| Crosslinked polyvinylpyrrolidone | 5-7% |
| Glycerin | 30-35% |
| Propylene glycol | 12-18% |
| Ethylene oxide, propylene oxide block co-polymer, avg. MW >5 kDa | 5-10% |
| Polyethylene glycol 600 | 5-15% |
| Crosslinked polyvinylpyrrolidone complexed with 15-25% $H_2O_2$ | 3-8% |
| Calcium pyrophosphate | 10-20%. |

The compositions may optionally comprise any or all of the following ingredient classes and/or particular ingredients by weight, each being based on the weight of the composition:

| Ingredient | Amount |
|---|---|
| Humectants 35-5%, e.g. | |
| Glycerin | 25-40%, e.g., about 30-35% |
| Propylene glycol | 10-25%, e.g., about 12-18% |
| Thickener/Rheology Modifiers, e.g. | |
| Polysorbate 20/Polysorbate 80 Propylene glycol Monocaprylate | 0.5-4%, e.g., about 1-3% |
| Crosslinked polyvinylpyrrolidone | 3-8%, e.g., about 5-7% |
| Polymers 10-25%, e.g., | |
| Ethylene oxide, propylene oxide block co-polymer, avg. MW >5 kDa | 5-10%, e.g., about 3-8% |
| Polyethylene glycol 600 | 5-15%, e.g., about 10% |
| Whitener, 3-10%, e.g., | |
| Crosslinked polyvinylpyrrolidone complexed with 15-25% hydrogen peroxide | 3-10%, e.g., about 5.5% |
| Abrasive, 5-25%, e.g. | |
| Calcium pyrophosphate | 10-20%, e.g., about 15% |
| Fluoride, 0-1%, e.g. | |
| Sodium monofluorophosphate | 0.5-1%, e.g., about 0.76% |
| Surfactant, e.g., SLS | 0-3% |
| Tartar control agent, e.g. TSPP | 0.5-5%, e.g., about 2% |
| Antioxidant, 0.01-5%, e.g. | |
| BHT | 0.03% |
| Flavorings | 0.1-5% |
| Water | <3% |

Methods are provided to whiten an oral surface in a human or animal subject comprising storing in stable form a composition of the invention, and contacting said composition with the oral surface. As used herein "animal subject" includes higher order non-human mammals such as canines, felines, and horses. The oral care composition is contacted with an oral surface of the mammalian subject to thereby whiten teeth in a highly efficacious manner, without any negative interaction between the whitening agent, the peroxide incompatible abrasive, and other ingredients.

In various embodiments, it is preferred that the oral care composition is applied and contacted with the oral surface. The dentifrice, prepared in accordance with particular embodiments of the invention, is preferably applied regularly to an oral surface, preferably on a daily basis, at least one time daily for multiple days, but alternately every second or third day. Preferably the oral composition is applied to the oral surfaces from 1 to 3 times daily, for at least 2 weeks up to 8 weeks, from four months to three years, or more up to lifetime.

The invention is illustrated in the following non-limiting examples.

EXAMPLES

Comparative Example 1

A dentifrice was prepared according to Comparative Example 1. The composition had the following ingredients as specified in Table 2, in which the amounts are in wt %:

TABLE 2

| Ingredient | Comp. Ex. 1 | Example 1 | Example 2 | Example 3 | Comp. Ex. 2 | Comp. Ex. 3 |
|---|---|---|---|---|---|---|
| $PEG_{118}/PPG_{66}$ co-polymer (Pluracare L1220F) | 7.5 | 7 | 7 | 7 | 7 | 9 |

TABLE 2-continued

| Ingredient | Comp. Ex. 1 | Example 1 | Example 2 | Example 3 | Comp. Ex. 2 | Comp. Ex. 3 |
|---|---|---|---|---|---|---|
| Glycerin | 33.36 | 32.36 | 32.36 | 32.36 | 32.36 | 32.36 |
| Propylene glycol | 15 | 14.5 | 14.5 | 14.5 | 14.5 | 14.5 |
| PEG 600 | 10 | 10 | 10 | 10 | 12 | 10 |
| Crosslinked PVP thickener | 6 | 6 | 6 | 6 | 6 | 6 |
| Crosslinked PVP/$H_2O_2$ | 5.5 | 5.5 | 5.5 | 5.5 | 5.5 | 5.5 |
| Calcium pyrophosphate | 15 | 15 | 15 | 15 | 15 | 15 |
| TSPP | 2 | 2 | 2 | 2 | 2 | 2 |
| Sucralose | 0.05 | 0.05 | 0.05 | 0.05 | 0.05 | 0.05 |
| Sodium saccharin | 0.6 | 0.6 | 0.6 | 0.6 | 0.6 | 0.6 |
| Sodium monofluorophosphate | 0.76 | 0.76 | 0.76 | 0.76 | 0.76 | 0.76 |
| Sodium lauryl sulfate | 2 | 2 | 2 | 2 | 2 | 2 |
| BHT | 0.03 | 0.03 | 0.03 | 0.03 | 0.03 | 0.03 |
| 85 wt % syrupy phosphoric acid | 0.2 | 0.2 | 0.2 | 0.2 | 0.2 | 0.2 |
| Mint flavor | 2 | 2 | 2 | 2 | 2 | 2 |
| Polyethylene glycol monocaprylate | — | 2 | — | — | — | — |
| Polysorbate 20 | — | — | 2 | — | — | — |
| Polysorbate 80 | — | — | — | 2 | — | — |
| Total | 100 | 100 | 100 | 100 | 100 | 100 |

The dentifrice of Comparative Example 1 comprises a thickening system comprising 6 wt % crosslinked polyvinylpyrrolidone. The dentifrice of Comparative Example 1 represents compositions which employ polyvinyl pyrrolidone, in a whitening dentifrice additionally comprising crosslinked PVP/$H_2O_2$ as a whitening active together with a substantially anhydrous vehicle comprising $PEG_{118}/PPG_{66}$ co-polymer (Pluracare L1220F), glycerin, propylene glycol and PEG 600 together with calcium pyrophosphate and TSPP.

The rheological properties of the dentifrice of Comparative Example 1 were measured to determine the viscosity/shear stress rheology profile. The data from the rheology profile was employed to calculate the pressure required to pump the composition of Comparative Example 1 through a pipe 87 meters long having an internal diameter of 100 mm at a flow rate of 1100 cm³/second. This calculation was carried out to simulate production conditions during commercial manufacture of the dentifrice.

The results are shown in Table 3.

TABLE 3

| | Comp. Ex. 1 | Example 1 | Example 2 | Example 3 | Comp. Ex. 2 | Comp. Ex. 3 |
|---|---|---|---|---|---|---|
| Pressure (bar) | 20.4 | 14.6 | 12.4 | 13.0 | 18.7 | 18.6 |

Table 3 shows that the calculated pumping pressure for Comparative Example 1 is 20.4 bar. This compares to a desired maximum pumping pressure of less than 18 bar, even more desired 15 bar, in the simulated production conditions. Consequently, it must be concluded that the dentifrice of Comparative Example 1 has poor rheology, and would be difficult to pump during manufacture.

Without being bound by any theory, it is believed that the composition of Comparative Example 1, which contains no gum, has a viscosity which is primarily caused by friction among space filler such as the crosslinked PVP and abrasive particles, and so has a high dynamic shear yield stress.

Examples 1 to 3

A number of gel dentifrices were prepared according to Examples 1 to 3 which are examples of the compositions of the invention. The compositions have the ingredients as specified in Table 2.

The dentifrice of Example 1 comprised the same thickening system comprising 6 wt % crosslinked polyvinylpyrrolidone but additionally comprised 2 wt % propylene glycol monocaprylate as a nonionic rheology modifier. The remaining ingredients were the same as for the dentifrice of Comparative Example 1 and the amounts thereof were substantially the same, but modified slightly to accommodate the addition of the nonionic rheology modifier, as for the dentifrice of Comparative Example 1.

The rheological properties of the dentifrice of Example 1 were measured as discussed above for Comparative Example 1 to determine the viscosity/shear stress rheology profile. The data from the rheology profile was employed to calculate the pressure required to pump the composition of Example 1 through a pipe 87 meters long having an internal diameter of 100 mm at a flow rate of 1100 cm³/second. This calculation was carried out to simulate production conditions during commercial manufacture of the dentifrice. The results are shown in Table 3.

Table 3 shows that the calculated pumping pressure for Example 1 was 14.7 bar. This is less than the more desired maximum pumping pressure of 15 bar in the simulated production conditions. Consequently, the dentifrice of Example 1 has good rheology and can readily be pumped during manufacture.

The dentifrice of Example 2 comprised the same thickening system as Example 1; only the nonionic rheology modifier was changed, and this comprised 2 wt % polysorbate 20 as a nonionic rheology modifier. The remaining ingredients and amounts thereof were the same as for the dentifrice of Example 1.

The rheological properties of the dentifrice of Example 2 were measured as discussed above for Example 1 to determine the viscosity/shear stress rheology profile. The data from the rheology profile was again employed to calculate the pressure required to pump the composition of Example 2 as described above for Example 1. Table 3 shows that the calculated pumping pressure for Example 2 was 12.4 bar. This is less than the more desired maximum pumping pressure of 15 bar in the simulated production conditions. Consequently, the dentifrice of Example 2 has good rheology and can readily be pumped during manufacture.

The dentifrice of Example 3 comprised the same thickening system as Example 1; only the nonionic rheology modifier was changed, and this comprised 2 wt % polysorbate 80 as a nonionic rheology modifier. The remaining ingredients and amounts thereof were the same as for the dentifrice of Example 1.

The rheological properties of the dentifrice of Example 3 were measured as discussed above for Example 1 to determine the viscosity/shear stress rheology profile. The data from the rheology profile was again employed to calculate the pressure required to pump the composition of Example 3 as described above for Example 1. Table 3 shows that the calculated pumping pressure for Example 2 was 13.0 bar. This is less than the more desired maximum pumping pressure of 15 bar in the simulated production conditions. Consequently, the dentifrice of Example 3 has good rheology and can readily be pumped during manufacture.

In addition, the dynamic yield shear stress of the composition of each of Examples 1 to 3 was measured, and the results were as follows: Example 1, 9.1 bar; Example 2, 5.8 bar; and Example 3, 8.0 bar. These dynamic yield shear stress values show that the compositions yield in shear when pumped at a relatively low pressure, which is lower than a typical pumping pressure during manufacture. Consequently, the addition of the nonionic rheology modifier has lowered the dynamic yield shear stress of the compositions, causing shear thinning when pumped and so rendering them readily pumpable.

Without being bound by any theory, it is believed that by adding the nonionic rheology modifier to the composition of Examples 1 and 3, which contain no gum, the friction among space filler such as the crosslinked PVP and abrasive particles is reduced, thereby lowering the viscosity at high shear, by providing lubrication to the space filler in the composition. This correspondingly reduces the dynamic yield shear stress of the compositions.

Comparative Examples 2 and 3

The dentifrices of Comparative Examples 2 and 3 comprised a thickening system comprising 6 wt % crosslinked polyvinylpyrrolidone. Instead of adding a nonionic rheology modifier in accordance with the invention, and Examples 1 to 3, as compared to Comparative Example 1 the composition of Comparative Example 2 had 2 wt % increased polyethylene glycol 600 and the composition of Comparative Example 3 had 2 wt % increased ethylene oxide, propylene oxide block co-polymer.

The rheological properties of the dentifrices of Comparative Examples 2 and 3 were measured as for Examples 1 to 3 and the results are shown in Table 3.

The dentifrice of Comparative Example 2 had a simulated pumping pressure which was high at 18.7 bar. Consequently, it must be concluded that the dentifrice of Comparative Example 2 has poor rheology, and would be difficult to pump during manufacture.

The dentifrice of Comparative Example 3 had a simulated pumping pressure which was high at 18.6 bar. Consequently, it must be concluded that the dentifrice of Comparative Example 3 has poor rheology, and would be difficult to pump during manufacture.

The data described in the Examples evidences the unexpected improvement in rheology, in particular the ability to be pumped during manufacture while retaining cosmetic stability, of the whitening compositions of the invention. Specifically, it is unexpected that the addition of a liquid (e.g. propylene glycol or an ethylene oxide/propylene oxide block co-polymer) does not necessarily solve the problem, even though you would expect the liquid to reduce the viscosity of the formulation.

While particular embodiments of the invention have been illustrated and described, it will be obvious to those skilled in the art that various changes and modifications may be made without departing from the scope of the invention as defined in the appended claims.

We claim:

1. An oral care composition comprising (i) a whitening complex comprising crosslinked polyvinylpyrrolidone complexed with hydrogen peroxide, and (ii) a thickening agent comprising a crosslinked polyvinylpyrrolidone, the composition further comprising (iii) a nonionic rheology modifier selected from at least one of a polysorbate surfactant and an alkylene glycol ester of a $C_6$-$C_{12}$ fatty acid, or a mixture thereof.

2. The composition of claim 1 wherein the polysorbate surfactant is selected from polysorbate 20 and polysorbate 80, or a mixture thereof.

3. The composition of claim 1 wherein the alkylene glycol ester of a $C_6$-$C_{12}$ fatty acid comprises a propylene glycol ester of a $C_6$-$C_{12}$ fatty acid.

4. The composition of claim 3 wherein the alkylene glycol ester of a $C_6$-$C_{12}$ fatty acid comprises an alkylene glycol ester of caprylic acid.

5. The composition of claim 4 wherein the alkylene glycol ester of caprylic acid comprises propylene glycol monocaprylate.

6. The composition of claim 1 wherein the nonionic rheology modifier comprises from 0.5 to 4 wt % based on the weight of the composition.

7. The composition of claim 6 wherein the nonionic rheology modifier comprises from 1 to 3 wt % based on the weight of the composition.

8. The composition of claim 7 wherein the nonionic rheology modifier comprises about 2 wt % based on the weight of the composition.

9. The composition of claim 1 wherein the crosslinked polyvinylpyrrolidone thickening agent is present in an amount of from 3 wt % to 8 wt % based on the weight of the composition.

10. The composition of claim 9 wherein the crosslinked polyvinylpyrrolidone thickening agent is present in an amount of from 5 wt % to 7 wt % based on the weight of the composition.

11. The composition of claim 1 wherein the crosslinked polyvinylpyrrolidone thickening agent is present in an amount of from 5 wt % to 7 wt % based on the weight of the composition, the nonionic rheology modifier comprises from 1 to 3 wt % based on the weight of the composition, and the total weight of the crosslinked polyvinylpyrrolidone thickening agent and the nonionic rheology modifier is from 7 wt % to 9 wt % based on the weight of the composition.

12. The composition of claim 1 further comprising an ethylene oxide, propylene oxide block co-polymer of average molecular weight greater than 5000 Da, being substantially free of an ethylene oxide, propylene oxide block co-polymer of average molecular weight less than 5000 Da.

13. The composition of claim 12 wherein the ethylene oxide, propylene oxide block co-polymer comprises (ethylene oxide)$_x$-(propylene oxide)$_y$ wherein x is an integer of 80-150 and y is an integer 30-80.

14. The composition of claim 12 wherein the ethylene oxide, propylene oxide block co-polymer is present in an amount of from 5 wt % to 10 wt % based on the weight of the composition.

15. The composition of claim 1 wherein the crosslinked polyvinylpyrrolidone complexed with hydrogen peroxide is present in an amount of from 3 wt % to 8 wt % based on the weight of the composition.

16. The composition of claim 1 wherein the whitening complex contains 10-30 wt % hydrogen peroxide and 5-15 wt % total nitrogen, based on the weight of the whitening complex.

17. The composition of claim 1 wherein the total amount of hydrogen peroxide is from 0.5 wt % to 3 wt % based on the weight of the composition.

18. The composition of claim 1 further comprising polyethylene glycol of average molecular weight 400 to 800 Da.

19. The composition of claim 18 wherein the polyethylene glycol is present in an amount of from 5 wt % to 15 wt % based on the weight of the composition.

20. The composition of claim 1 further comprising at least one humectant selected from glycerin and propylene glycol, or a mixture thereof.

21. The composition of claim 20 wherein the at least one humectant is present in an amount of from 35 wt % to 50 wt % based on the weight of the composition.

22. The composition of claim 21 wherein the at least one humectant is present in an amount of from 40 wt % to 45 wt % based on the weight of the composition.

23. The composition of claim 20 comprising propylene glycol in an amount of from 10 wt % to 25 wt % based on the weight of the composition.

24. The composition of claim 20 comprising glycerin in an amount of from 25 wt % to 40 wt % based on the weight of the composition.

25. The composition of claim 1 which contains less than 3 wt % water based on the weight of the composition.

26. The composition of claim 1 which is a toothpaste comprising a calcium pyrophosphate abrasive.

27. The composition of claim 26 wherein the calcium pyrophosphate is present in an amount of from 10 wt % to 40 wt % based on the weight of the composition.

28. The composition of claim 1 comprising the following ingredients by weight, each being based on the weight of the composition:

| | |
|---|---|
| a. Nonionic rheology modifier | 1-3% |
| b. Crosslinked polyvinylpyrrolidone | 5-7% |
| c. Glycerin | 30-35% |
| d. Propylene glycol | 12-18% |
| e. Ethylene oxide, propylene oxide block co-polymer, avg. MW >5 kDa | 5-10% |
| f. Polyethylene glycol 600 | 5-15% |
| g. Crosslinked polyvinylpyrrolidone complexed with 15-25% $H_2O_2$ | 0.5-16.5% |
| h. Calcium pyrophosphate | 10-40% |

29. The composition of claim 1 further comprising an anionic surfactant in an amount of from 0.5 to 3 wt % based on the weight of the composition.

30. The composition of claim 29 wherein anionic surfactant and the nonionic rheology modifier constitute the sole surfactants in the composition.

31. A method of tooth whitening comprising applying the composition of claim 1 to the surface of a mammalian tooth.

* * * * *